United States Patent
Nguyen et al.

(10) Patent No.: US 6,504,957 B2
(45) Date of Patent: Jan. 7, 2003

(54) METHOD AND APPARATUS FOR IMAGE REGISTRATION

(75) Inventors: Van-Duc Nguyen, Albany, NY (US); Victor Nzomigni, Niskayuna, NY (US); Charles Vernon Stewart, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/085,158

(22) Filed: Feb. 27, 2002

(65) Prior Publication Data

US 2002/0118892 A1 Aug. 29, 2002

Related U.S. Application Data

(60) Division of application No. 09/303,241, filed on Apr. 30, 1999, and a continuation-in-part of application No. 08/889,070, filed on Jul. 7, 1997, now abandoned.

(51) Int. Cl.[7] ................................................. G06K 9/62
(52) U.S. Cl. ...................... 382/209; 382/141; 382/209; 382/218; 382/219; 345/216; 345/218; 348/36; 348/87; 356/394
(58) Field of Search ................................. 382/100, 103, 382/106, 141, 145, 149–150, 154, 209, 218, 224, 270, 282, 284, 291, 294, 296; 348/36, 87, 590; 356/237, 239, 371, 394; 345/216, 218

(56) References Cited

U.S. PATENT DOCUMENTS

| | | | |
|---|---|---|---|
| 5,081,689 A | 1/1992 | Meyer et al. | 382/22 |
| 5,282,143 A | 1/1994 | Shirai et al. | 700/187 |
| 5,546,475 A | 8/1996 | Bolle et al. | 382/190 |
| 5,640,200 A * | 6/1997 | Michael | 348/87 |
| 5,668,631 A | 9/1997 | Norita et al. | 356/376 |
| 5,822,742 A | 10/1998 | Alkon et al. | 706/31 |
| 5,850,466 A * | 12/1998 | Schott | 382/141 |
| 5,850,469 A * | 12/1998 | Martin et al. | 382/154 |
| 5,859,698 A * | 1/1999 | Chau et al. | 356/237 |
| 5,970,166 A * | 10/1999 | Nichani | 382/141 |
| 5,990,901 A | 11/1999 | Lawton et al. | 345/429 |
| 6,018,349 A | 1/2000 | Szeliski et al. | 345/425 |
| 6,041,138 A | 3/2000 | Nishida | 382/197 |

(List continued on next page.)

OTHER PUBLICATIONS

"Closed–Form Solution of Absolute Orientation Using Unit Quaternions" by B. Horn, Journ. of Opt. Soc. Amer., 4(4); 629–642, 1987, [15].

"Computational Geometry for Design and Manufacture" by I.D. Faux and M.J. Pratt, (Ellis Hornwood, Ltd., p. 79 (1979), Chichester [8, p. 72]).

*Primary Examiner*—Jose L. Couso
*Assistant Examiner*—Gregory Desire
(74) *Attorney, Agent, or Firm*—Jean K. Testa; Patrick K. Patnode

(57) ABSTRACT

A machine vision system includes an apparatus for registering an input image of an object, such as an aircraft engine blade, to a reference image comprising ideal specifications for the object in order to detect flaws in the object. The system includes one or more imaging devices for obtaining the input image representing the object. The system further includes a processor for registering the input image to the reference image. The processor includes a patch determining device for identifying low curvature portions of the reference image off-line. A transformation estimator matches the low curvature portions of the reference image to corresponding low curvature portions of the object, and provides a transformation matrix which maps points on the reference image 11 to corresponding points on the input image for precise and fast registration.

4 Claims, 2 Drawing Sheets

U.S. PATENT DOCUMENTS

| | | | | |
|---|---|---|---|---|
| 6,064,749 A | * | 5/2000 | Hirota et al. | 382/103 |
| 6,072,903 A | | 6/2000 | Maki et al. | 382/190 |
| 6,100,894 A | | 8/2000 | Goel | 345/423 |
| 6,118,893 A | * | 9/2000 | Li | 382/150 |
| 6,128,046 A | * | 10/2000 | Totsuka et al. | 348/590 |
| 6,134,340 A | | 10/2000 | Hsu et al. | 382/124 |
| 6,157,747 A | * | 12/2000 | Szeliski et al. | 382/284 |
| 6,269,194 B1 | * | 7/2001 | Nichani | 382/270 |
| 6,295,374 B1 | * | 9/2001 | Robinson et al. | 382/218 |
| 6,400,828 B2 | * | 6/2002 | Covell et al. | 382/100 |

* cited by examiner

METHOD AND APPARATUS FOR IMAGE REGISTRATION

CROSS REFERENCE TO RELATED APPLICATIONS

This application is a division of application Ser. No. 09/303,241, filed Apr. 30, 1999, which is hereby incorporated by reference in its entirety.

This application is a continuation-in-part of application Ser. No. 08/889,070, filed Jul. 7, 1997 now abandoned.

The US Government may have certain rights in this invention pursuant to contract number 70NANB5H 1085 awarded by the National Institute of Standards and Technology (NIST).

BACKGROUND OF THE INVENTION

This invention relates to machine vision systems, and more particularly to an image registration method and apparatus for accurately registering an object to be inspected to reference data in order to detect flaws in the object.

Machine vision technology addresses the problem of detecting flaws in objects by analyzing flaws in images obtained from the objects. An image is deemed to be flawed when it does not accurately represent the object it was intended to represent. If the object is flawed, such as might result from wear and tear on the object, or an error in manufacturing the object, a flawed image results. In this case, the flawed image may accurately represent the flawed object, but nevertheless deviates from the image of what an unflawed object would be.

Most of the existing optical defect and flaw detection tools in the electronics manufacturing industry and many in other industries are based on an image-to-reference comparison scheme whereby a digitized product image is compared to some kind of reference data to detect abnormalities. Golden Template Comparison (GTC) is one such machine vision technique commonly employed to detect flaws and defects in images of 2-dimensional scenes that do not suffer from geometric distortion. According to this technique, an image of an object to be tested for flaws is compared to a "golden template", or reference image. A golden template image is the mean of a plurality of good sample images. To perform the comparison, the input image and the golden template image must be registered with each other, and then subtracted. The resulting difference image is then analyzed for features that indicate flaws or defects in the test object.

In practice, it is found that the quality of the reference image and the accuracy of the registration step are major determinants of the performance of image-to-reference comparison systems. There exist conventional registration devices which register 3 dimensional reference images with images obtained from 3 dimensional test objects. These devices operate by obtaining and analyzing the input image to find identifying features of the imaged object. Identifying features of an object are high-curvature areas of the object such as corners, edges, and holes. The high curvature areas are then matched to the reference image, or vice versa, usually by techniques which calculate normals to the high curvature surfaces.

Alternatively, the object may be scanned to locate high-curvature areas and an input image of the high curvature areas created. The input image is then compared to the reference image to match structures on the reference image with identifying features of the object. Differences in location and orientation the reference image and corresponding identifying features of the input image are identified. Once these differences are found, a rotation matrix is used to update the orientation, or pose, of the reference image, the input image, or both. This process is repeated until there is less than an acceptable amount of misregistration. This approach is also typically implemented by determining normals to high curvature surface areas.

Determination of surface normals has a high degree of error for high curvature surfaces since methods of creating an input image of the object's surface have a large degree of error at high curvature locations. Also, determination of the location and normal vectors for a large number of structures can become computationally burdensome.

Currently, there is a need for a system which efficiently and accurately registers an object's input image to a corresponding reference image of the object.

BRIEF SUMMARY OF THE INVENTION

A system for registering an input image to a reference image includes one or more imaging devices for obtaining an input image and a processor for comparing the image to the reference image. The processor includes a patch determining device for identifying low curvature portions of the reference image, and for matching the low curvature portions of the reference image to corresponding low curvature portions of the input image.

A transformation estimator provides a transformation matrix which maps points on the reference image 11 to corresponding points on the input image for registration.

BRIEF DESCRIPTION OF THE DRAWINGS

While the novel features of the invention are set forth with particularity in the appended claims, the invention, both as to organization and content, will be better understood and appreciated, along with other objects and features thereof, from the following:

DETAILED DESCRIPTION OF THE INVENTION

Figure 1:
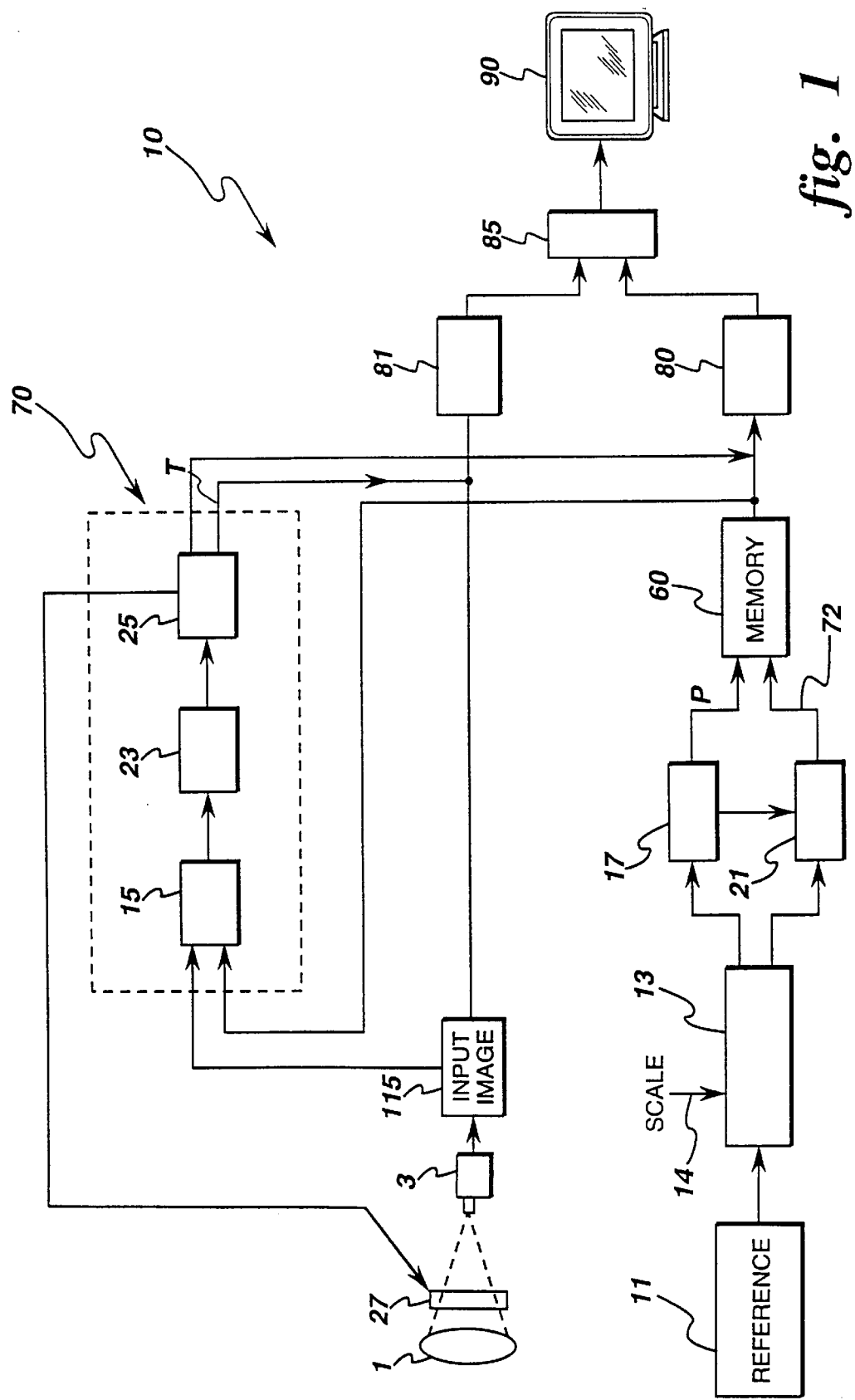
FIG. 1 is a block diagram of an embodiment of a machine vision system according to the present invention.

The following terms are defined as used herein. An image is defined herein to be a collection of data representing properties, design specifications, or attributes of an object. For example, a data collection which represents the 3 spatial dimensions (x, y, z) of an object is an image of the object. When such data is obtained by measuring the object and storing the measurements in memory, the stored measured data is referred to herein as an input image. The data comprising a Computer Assisted Drawing (CAD) of an object is an image of an object. CAD data comprising specifications for an object to which the object will be compared for purposes of flaw detection are referred to herein as a reference image. An image can further include a fourth dimension. This would occur for example, when imaging time changing objects and structures such as the human heart. The present invention, however, is not limited to three, or even four dimensional representations of objects. On the contrary, the apparatus and methods described herein are capable of representing objects in any number of dimensions, i.e. N-dimensional.

As used in this specification, the term object is not intended to be limited to refer to a physical object. An object can also be a non-physical object, such as a plan or process. An image of such an object is an N dimensional account of the attributes of the plan or process. For example, an object which is a financial model may be represented in 4 dimensions. The dimensions may be the attributes of the financial model, i.e., interest, principle, loan type, and time. Such a financial model may be imaged in terms of its corresponding 4 dimensional data, registered to a reference image comprising ideal values in accordance with the principles of the present invention, and the differences detected and displayed to an operator.

Each array element of an image is referred to herein as a pixel. A pixel represents a measurement or property at a given position in the scene. A pixel can represent measurements of the object's color, brightness, or distance of the object from the measuring device. A digitized input image is defined to be a digital reproduction of an object produced by measuring the object with a measuring device, such as by light rays (camera).

Mapping is the process of relating pixels in the output or displayed image to pixels in the input image. Mapping is accomplished by use of a deformation "model". Mapping may be computed by fitting a function to control point locations. Control points are features located in the input image whose location in the final output is known. Control points are located both in the input and the reference images. A model is a function which maps points in the input image to points in the output image. Mapping may be computationally expensive to apply. The models may be quite complex, involving long sequences of equations and iterative steps. A typical technique to overcome the complexity problem is to define a grid on the output image and map only the grid points by the model. All other points are found by interpolation within the grid. Thus the mapping process is simpler and less expensive.

For purposes of this specification, a patch is defined to be a grid on the reference image which encompasses at least a portion of the surface of the imaged object. The dimensions of the patch depend on the order of the deformation model.

Pose is defined to be the spatial orientation of an object with respect to a given viewpoint.

Alignment, or pose correction, is defined as orientation of a first object with respect to a second object so as to make at least one alignment parameter of the first object, such as planar position or angular orientation, substantially equal to the corresponding alignment parameter of the second object.

Registration is defined as the process of aligning an input image with a reference image. The registration process generally comprises two steps. First, determining corresponding points, or features of the input image and the reference image. Second, transforming the input and reference image to a common coordinate system. The transformation is typically geometric and includes translations, rotations, and scale changes. In other words, registration is the process of positioning two images of the same object with respect to one another so that corresponding points in the images represent the same point on the object. Registration involves orienting a first object with respect to a second object so as to make all alignment parameters of the first object substantially equal to the corresponding alignment parameters. In that sense, alignment, or pose correction, can be defined as imprecise registration. For example, an alignment step for coarse relative positioning can be followed by a registration step to achieve fine, or more precise relative positioning.

Pose error is defined to be the difference between the position of the object as represented in the input image of the object, and the position of the object as represented in the reference image of the object. In that sense, pose correction is repositioning the object such that the pose error is minimized.

Interpolation is defined to mean estimation of the values between two known values. The problem of accuracy is common to all transformations. On any grid, any geometric transformation results generally in points that do not any longer lie on the original grid. Therefore suitable algorithms are required to interpolate the values at transformed points from the neighboring pixels. The high demands for position accuracy make image interpolation critical.

Matching is defined to mean post-registration comparison of a reference image with an input image, or vice versa, to determine differences which represent deviations of the input image from the reference image, or of the object's actual shape from it's ideal, or specified shape.

FIG. 1 is a block diagram of a machine vision system 10 according to one embodiment of the present invention. An object to be inspected 1, is positioned within the sensing range of an imaging device 3. In one embodiment of the invention, imaging device 3 operates off-line to obtain input image 115 and store it for further processing at a later time. In another embodiment imaging device 3 operates in real time. In one embodiment of the invention the object to be inspected 1 is an aircraft engine blade, and imaging device 2 is a hard gauge comprising micrometers, calipers, and shims. The hard gage measures a plurality of defined contact points on the blade to characterize the blade. In this embodiment, the stored measurements comprise digitized input image 115. In another embodiment of the invention, imaging device 2 is a coordinate measurement machine (CMM) which translates and rotates a probe to sample points on the surface of object 1. CMMs provide dense measurements of the sample points. However, the time to scan an object, such as an aircraft engine blade, using CMMs is unsatisfactory for many applications.

Yet another embodiment of the invention employs a full-field non contact range sensor as an imaging device 3. The range sensor scans the external surfaces of object 1 about 100 times faster than a CMM. Range sensors, such as range cameras, take images similar to ordinary cameras except that, instead of measuring the visible light irradiated by an object, a range camera measures the distance from the camera to the surface of the object. Thus the image provided by a range camera is referred to as a range image. Full field, non contact range sensors currently available include Integrated Automation Systems' (IAS) 4DI model sensors which are based on laser line grating and stereo triangulation. Another suitable range sensor is available from Cyber-Optics Co. These sensors are based on single laser line scan and rotation of the object.

The advantage of using range cameras over fully three-dimensional imaging devices like X-ray machines is that range cameras are cheaper, safer, much easier to use, and can simultaneously acquire a color image of the scene. However, for all their advantages, range cameras cannot see through an object like an X-ray machine can and, accordingly, several range images of the object must be taken from different vantage points to acquire the complete surface description of the object.

As those of ordinary skill in the art will recognize, other data collection devices and imaging devices, such as x-ray and Magnetic Resonance Imaging (MRI)I devices can provide an input image in accordance with the present invention. Accordingly, the invention is not intended to be limited to data collection devices, or imaging devices which provide range images.

The three dimensional data which represents the measurements obtained from object 1 are stored in memory as input image 115. In an alternative embodiment of the present invention input image data is provided directly to a geometry determining device 15.

As shown in FIG. 1, a reference image 11 comprises template specifications, in the form of digital data, to which the input image 115 of object 1 will be compared in order to detect defects in object 1. Template specifications are ideal characteristics of object 1. There exist several types of reference images suitable for use in the present invention. Among them are reference images created off-line, reference images derived from other product areas of identical pattern, reference images derived from known defect-free products, and reference images generated from design data, such as CAD models. A CAD model typically represents a scene in terms of a grid. Each section of the grid comprises a portion of the scene containing the object of interest.

According to the present invention, a patch determining device 13 portions reference image 11 into a plurality of surface areas, referred to herein as patches. Patch determining device 13 comprises a processor programmed to perform the operations described herein and memory for storing patch data. A patch can include one or more sections of a grid of a CAD image, and portions thereof. In one embodiment of the invention the number of patches into which reference image 11 is portioned is manually selected by an operator as indicated at 14 in FIG. 2. The more patches selected the smaller will be the area of each patch, and conversely, the fewer patches selected the larger will be the area of each patch. Larger patches provide course registration of object 1 to reference image 11 and smaller patches allow for finer the registration of object 1 to reference image 11.

In one embodiment of the invention, patch determining device 13 operates independently of the other elements of system 100. In other words, patch determining device 13 computes low curvature patches off-line and stores the low curvature patches in memory 60 for registration with object 1 at a later time. Based on the patch scale selected by the operator, the reference image is digitized at regular grid points on the CAD image grid which fall within each patch. The local curvature of grid points within each patch is checked, and those patches containing grid points having curvature minima are retained. In one embodiment of the invention, a least square error technique is utilized to check local curvature. Thus a set of low curvature patches is obtained for the selected scale. Each selected low curvature patch represents a low curvature surface portion of reference image 50. The scale may be varied by the operator such that a plurality of patch sets, each set corresponding to a different patch size, or scale, is obtained and stored. In this manner, course to fine registration of object 1 to reference image 11 may be achieved quickly on line.

Each patch Pi is represented in patch point memory 60 by its center position pi and its normal ni. A patch center device 17 calculates a center point $p_i$ for each low curvature surface patches $P_i$. In one embodiment of the invention, the center point p of a patch is defined to be it's center of mass. As those of ordinary skill in the art will recognize, other schemes for representing patches may be devised, including schemes which define center point differently. These are intended to remain within the scope of the present invention. A normal vector calculation device 21 determines a vector $n_i$ normal to each patch $P_i$ at its center point $p_i$. Point pairs $p_i$, $n_i$ are then stored in patch point memory 60.

Transformation estimator 70 provides at an output, a transformation matrix T which is a mapping of points in reference image 11 to corresponding points in input image 115. Transformation estimator 70 comprises a geometry determining device 15, a distance minimizer 23 and a rotation converter 25. Geometry determining device 15 analyzes a plurality of patches stored in patch point memory 60. For each patch center point p, geometry determining device 15 determines a corresponding point q on a corresponding patch P' of input image 115. Input image 115 comprises data representing measurements taken of the surface of object 1.

Geometry determining device 15 receives center location $p_i$ and normal $n_i$ for each of the patches $P_i$, and also receives input image 115.

Geometry determining device 15 determines where a geometric extension of the normal vector from point $p_i$ will intercept the surface data. This location is termed $q_i$, $q_i$ being the intersection point on the surface data from an extension of the normal of the ith patch.

Figure 2:
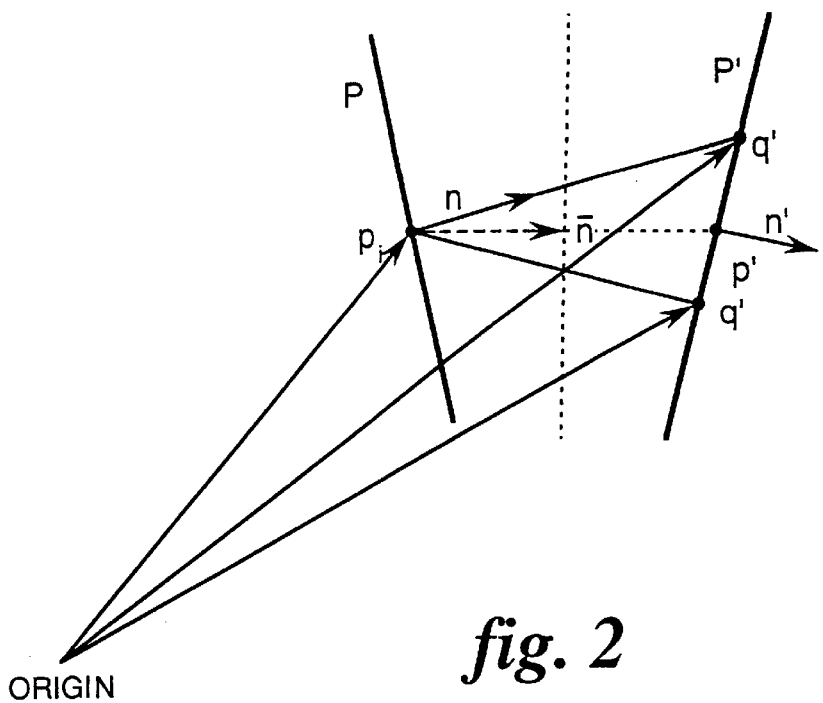
FIG. 2 is an illustration of a measure of distance between two 3D surfaces according to the present invention.

FIG. 2 illustrates the basic operations performed by geometric determination device 15, which, in one embodiment of the invention is a processor programmed to perform the operations illustrated in FIG. 2 and described hereinbelow. FIG. 2 shows a patch P of reference image 11 (best illustrated in FIG. 1) and a patch P' of input image 115. For point locations p on patches P of reference image 11, corresponding vectors n are determined, each vector $n_i$ being normal point $p_i$ relative to reference point O. In one embodiment of the invention point O is chosen to be the center of mass of reference image 11. For each patch $P_i$, geometric determination device 15 creates a ray $I_i$ along the normal vector $n_i$ and extends ray $I_i$ until ray $I_i$ intersects with input image 115. The intersection point is designated $q_i$. For each patch Pi geometry determining device 15 finds corresponding location qi by moving a matched filter, sized to Pi, along ray Ii, through pi and parallel to ni, searching for the nearest significant response from current location pi. This procedure estimates the intersection point of Ii with the surface of object 1, as represented by input image 115, without the expensive and noise sensitive process of estimating surface parameters from input image 115 itself.

A distance minimizer 23 receives vector $n_i$, center point $p_i$, and location $q_i$ for each of the patches $P_i$. Distance minimizer 23 minimizes each of the distances d(P,P') from the reference image patches to the input image patches. To accomplish this distance minimization device 23 receives $p_i$, $q_i$ and $n_i$ for each patch $P_i$ and determines the pose error between the reference image and the input image in terms of W, and t". W is a skew symmetric matrix which describes the cross-product between a 3-element rotation vector $$\omega = (\omega_x, \omega_y, \omega_z) = 2\tan\left(\frac{\theta}{2}\right)u, \text{ and either } p_i \text{ or } q_i;$$

wherein θ is the angle and u is the unit vector of the axis of rotation of the input image and the reference image.

Accordingly, in one embodiment of the invention, pose error is described by the following relationship:

$$\min_{W, t''} \sum_i [((I - W/2)q_i - (I + W/2)p_i - t'')^T n_i]^2$$

The incremental rigid transformation T=(R, t) is determined by rotation conversion device 25. Rotation conversion device 25 determines rotation intermediates (w, t"). Rotation conversion device 25 converts rotation intermediates (w, t") into pose error (R, t). Rotation conversion device 25 also provides pose error to an actuator 27, which is coupled to a mechanical device for adjusting the spatial orientation of object 1, if a physical object is used. Rotation conversion device 25 converts W, t" into an actual pose error rotation, R, and translation t. In one embodiment of the invention, the pose error may be provided to an offset device which provides an adjusted pose as input to reference image 11, causing the pose of the reference image to be adjusted. An alternate embodiment of the invention works by rotating both images toward each other by half of the total rotation. Thus, the offset device adjusts the pose of both the object and the reference image according to the pose error (R, t).

In yet another embodiment of the present invention, a weighting device 31 is coupled to object 1, and operates after a pose error (R, t) has been calculated. Weighting device 31 determines a weighting factor for a number of surface data points. The weighting factor becomes smaller as the distance of the point from the reference image surface becomes larger, and is a maximum when the surface data point coincides with its corresponding patch from the reference image 11. This effectively filters the surface data correcting for 'outlier' points which are incorrect due to real errors in their determination.

Since it is difficult to determine the exact corresponding point on one patch to another point on another patch, one embodiment of the present invention utilizes an approximate normal distance technique to speed up the process. A description of this process follows.

Figure 3:
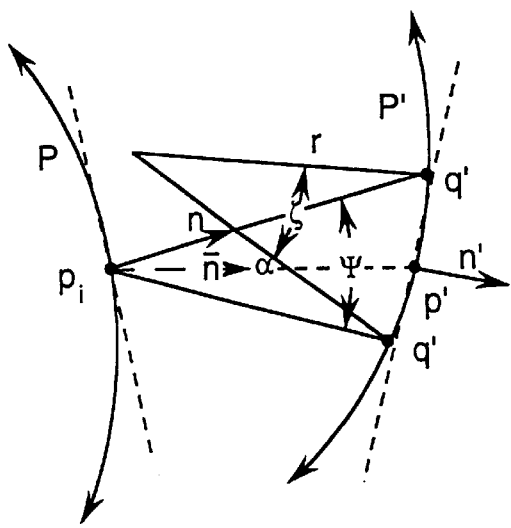
FIG. 3 is an illustration of the effect of curvature on approximating distance between a reference image and an input image.

Let r be the local radius of curvature at the patches P and P' as show in FIG. 3. Points q and q' are now on the curved patch P', and are found from mid point p of patch P, along the normals n and n' respectively. The distance measure between a curved patch and a curved surface, is defined as:

$$d(P, P')=(p'-p)^T n$$

A curved arc between points q and q' makes an angle y at the mid point p, and an angle z at the center of curvature of the patch P'.

$$d(P, P')^a ((q-p)^T n + rz^2/8)(\cos y/\cos(y/2))$$

$$^a((q'-p)^T n' + rz^2/8)/(\cos(y/2))$$

$$z^a y d(P, P')/r$$

The following approximate normal distance between low curvature patches and surfaces is used to avoid estimating local surface normal and curvature from range data:

$$d(P, P')^a (q-p)^T n$$

This approximation is valid when $y^a 0$ and $r >> |d(P, P')|$.

The distance between locations p and q along vector n is used as an approximation of the distance d(P, P) between the surface patches.

In order to limit computation processing and speed up on-line matching, a linear solution to pose is employed in one embodiment of the present invention. A linear solution of pose (Rodrigues formula) is described in: "Computational Geometry for Design and Manufacture" by I. D. Faux and M. J. Pratt, Ellis Hornwood, Ltd., p. 79 (1979).].

According to this technique, an object is rotated through an angle q about a unit vector axis u. The object is described in the 3-component vector w.

$$\omega = (\omega_x, \omega_y, \omega_z) = 2\tan\left(\frac{\theta}{2}\right)u$$

When rotation and translation are both involved, translation t is defined in terms of t".

According to this technique, an object is rotated through an angle q about a unit vector axis u. The object is described in the 3-component vector w.

$$\omega = (\omega_x, \omega_y, \omega_z) = 2\tan\left(\frac{\theta}{2}\right)u$$

When rotation and translation are both involved, translation t is defined in terms of t".

$$t''=t-\tfrac{1}{2}w\ddot{Y}t.$$

In one embodiment of the present invention, instead of rotating one object toward another, the object image and the reference image are each rotated half of the total rotation R toward each other.

$$R=(I-W/2)^{-1}(I+W/2)$$

Accordingly, rotation R can be split up into two terms in which both the reference image, and the input image may be rotated halfway toward each other. This is a linear solution. Since this linear solution is much less computationally burdensome than prior art techniques, the actual matching and rotation is performed more quickly.

In one embodiment of the invention, translation is defined in terms of W, t" as:

$$t=(I+W/2)t''.$$

Using the approximate normal distance described above and constructing $q_i$ (instead of $p'_i$) along the model normal $n_i$ (rather than the average normal $\bar{n}_i$), the approximate least squares pose error is:

$$\text{pose error} = W, t'' \sum_i [((I - W/2)q_i - (I + W/2)p_i - t'')^T n_i]^2$$

Since equation for pose error is a quadratic, it can be solved directly without iteration. Inputs are locations p and q, and normal vector n. The pose error equation results in W, t" which are intermediates used in determining the total rotation R.

W, and translation intermediate t" are used to solve for translation t.

Therefore, by minimizing pose error, the sum of the squared deviation in distance d(P, P') between reference image and the input image for all the patches, is minimized. This results in a quick and efficient method of registering the reference image to the input image.

In another alternate embodiment, the present invention solves for a rough pose, then weighting device 31 weights surface data point to reduce the effect of unreliable "outlier" points which are of questionable accuracy. A determination is made of how each measured point deviates from its local neighbors, for example, neighbors within a predefined radius, and this deviation is compared to a predetermined threshold. The predetermined threshold may be a statistical function of all, or a subset, of the data comprising input image 115. For example, the mean of the data may be used. A weight is determined for a plurality of the measured points, the greater the deviation, the lower the weight. The weighting value is designed to have a value of 1 when it coincides with a most desired location within the statistical grouping, and goes to 0 as the distance from this location increases. Many different weighting formulas will work with differing results. Each should have the characteristics as set forth above.

The pose is then again determined using the weighted data points as the surface data points.

A summary of the steps for the weighted embodiment is stated below:

1) using model and range data, solve for rough pose;
2) set model at rough pose;
3) determine deviation of a plurality of range points from the model surface;
4) attribute a weight, being between 1 and 0, to each data value based upon distance from model surface;
5) multiply each range data point by its weighting;
6) solve for fine pose from the rough pose, the model data, and the weighted range points.

While specific embodiments of the invention have been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. A method of comparing a theoretical N dimensional model surface to N dimensional measured data surface points of an object comprising the steps of:
    a) acquiring said N dimensional model;
    b) analyzing said model to determine a plurality of low curvature surface patches $P_i$, each $P_i$ having a curvature less than a predetermined curvature threshold;
    c) determining a surface normal vector $n_i$, and center location $p_i$ for each of said low curvature surface patches $P_i$;
    d) projecting a line from $p_i$ to intersect with location $q_i$ on the surface data;
    e) determining a pose error, being a sum of distances d(P, P') between locations $p_i$ and $q_i$ for a plurality of patches i;
    f) minimizing the sum of distances d(P, P') to result in the pose error;
    g) adjusting the pose of the N dimensional model relative to the N-dimensional data to according to the calculated pose error as a rough pose;
    h) calculating a statistical distribution of a plurality of data surface points;
    i) determining deviation from the calculated statistical distribution of a plurality of data surface;
    j) comparing the each of the plurality of data surface points to the statistical distribution;
    k) attributing a weight to each of the plurality of surface data points based upon the comparison to the statistical distribution, being between 1 and 0, with the weight going toward 0 as the distance from the center of the statistical distribution increases.
    l) multiplying each range data point by its weighting to result in weighted surface data;
    m) repeating steps (b) through (g) above to solve for fine pose using the weighted measured data in place of the original measured data;
    n) adjusting the rough pose of the N dimensional model relative to the N-dimensional surface data to according to the calculated pose error from the weighted measured data.

2. A system for adjusting pose registration between a theoretical N dimensional model surface to N dimensional measured data surface represented by the model comprising:
    a) a patch determination device for determining a plurality of patches $P_i$ each having less than a predetermined surface curvature;
    b) a patch center device functionally coupled to the patch determination device for calculating a center point $p_i$ for each of the plurality of low curvature surface patches;
    c) normal vector calculation device functionally coupled to the patch determination device and the patch center device for determining a vector $n_i$ normal to each patch $P_i$ at its center point $p_i$;
    d) a geometric determination device functionally coupled to the patch center, and normal vector calculation devices, and a surface data source, which extends the normal vector $n_i$ until it intersects with surface data at location $q_i$;
    e) a distance minimization device functionally coupled to the patch center, normal vector calculation and geometric calculation devices for determination of rotation intermediates ($\omega$, t");
    f) rotation conversion device coupled to the distance minimization device for receiving rotation intermediates (W, t") and for converting them into pose error (R, t); and
    g) an offset device coupled to the rotation conversion device, the surface data source and the model source, for receiving pose error (R, t) and adjusting the surface data and model pose according to the pose error (R, t).

3. The system for adjusting pose registration of claim 2, wherein the surface data source comprises:
    a) a physical object to be matched; and
    b) a ranging device which scans the surface of the object to provide surface data.

4. The system for adjusting pose registration of claim 3, further comprising a weighting device functionally coupled to the surface source device, the model source and distance minimization device for determining when a pose error (R, t) has been calculated and for determining a weighting factor which becomes smaller as the distance of the point from the model surface becomes larger, and is a maximum when the surface data point coincides with the model surface, for the plurality of surface points and multiplying each surface point by its weighting factor, then storing the weighted surface points in the memory.

* * * * *